(12) United States Patent
Asai et al.

(10) Patent No.: US 10,518,072 B2
(45) Date of Patent: Dec. 31, 2019

(54) NEEDLE-SHAPED BODY

(71) Applicant: TOPPAN PRINTING CO., LTD., Taito-ku (JP)

(72) Inventors: Ryoichi Asai, Taito-ku (JP); Tomoya Sumida, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/625,116

(22) Filed: Jun. 16, 2017

(65) Prior Publication Data

US 2017/0281919 A1 Oct. 5, 2017

Related U.S. Application Data

(63) Continuation of application No. PCT/JP2015/084774, filed on Dec. 11, 2015.

(30) Foreign Application Priority Data

Dec. 16, 2014 (JP) ................................. 2014-254318

(51) Int. Cl.
*A61M 37/00* (2006.01)

(52) U.S. Cl.
CPC . *A61M 37/0015* (2013.01); *A61M 2037/0023* (2013.01)

(58) Field of Classification Search
CPC ...... A61M 37/0015; A61M 2037/0023; A61M 2037/0046; A61M 2037/0061
See application file for complete search history.

(56) References Cited

U.S. PATENT DOCUMENTS

| | | | |
|---|---|---|---|
| 9,913,970 B2* | 3/2018 | Arami | A61M 37/0015 |
| 2012/0130207 A1 | 5/2012 | O'dea et al. | |
| 2013/0226098 A1* | 8/2013 | Tokumoto | A61M 37/0015 604/228 |
| 2014/0236090 A1* | 8/2014 | Colburn | A61M 37/0015 604/173 |
| 2015/0314117 A1 | 11/2015 | Arami et al. | |

FOREIGN PATENT DOCUMENTS

| | | |
|---|---|---|
| JP | 5285943 B | 9/2013 |
| WO | WO 2009/107806 A2 | 9/2009 |
| WO | WO 2012/046816 A1 | 4/2012 |
| WO | WO 2014/097837 A1 | 6/2014 |

OTHER PUBLICATIONS

International Search Report dated Mar. 8, 2016 in PCT/JP2015/084774, filed Dec. 11, 2015.

* cited by examiner

*Primary Examiner* — Laura A Bouchelle

(74) *Attorney, Agent, or Firm* — Oblon, McClelland, Maier & Neustadt, L.L.P.

(57) ABSTRACT

A needle-shaped body including a support section having a tubular shape with a center axis being a reference line, the support section having a proximal end and a distal end, a support substrate positioned in the support section and movable in a direction along the reference line, a needle section positioned on a main surface of the support substrate and protruding in a direction from the proximal end toward the distal end, a connecting section that detachably attaches the support substrate to the support section, and a guiding section that guides the support substrate along the reference line.

20 Claims, 10 Drawing Sheets

NEEDLE-SHAPED BODY

CROSS-REFERENCE TO RELATED APPLICATIONS

The present application is a continuation of International Application No. PCT/JP2015/084774, filed Dec. 11, 2015, which is based upon and claims the benefits of priority to Japanese Application No. 2014-254318, filed Dec. 16, 2014. The entire contents of these applications are incorporated herein by reference.

BACKGROUND OF THE INVENTION

Field of the Invention

The present invention relates to a needle-shaped body used by being pierced into the skin.

Discussion of the Background

Transdermal absorption method is known as a method for administering drug into the body by permeating the drug through the skin. In order to improve the efficiency of drug absorption into the body, a technique that uses a needle-shaped body having a needle section of a micrometer order to pierce the skin for direct drug administration into the skin has attracted attention.

As a needle-shaped body for use in such a transdermal absorption method, a configuration for example described in PTL 1 has been known.

The needle-shaped body described in PTL 1 includes the needle section formed in the needle section area on the first surface of the substrate (support substrate), and the piercing target housing section formed in the area surrounding the needle section area.

A through hole, for example, is formed inside or in the vicinity of the needle section. Through this through hole, bodily fluids can be collected or drugs can be supplied.

PTL 1: JP-B-5285943

SUMMARY OF THE INVENTION

According to an aspect of the present invention, a needle-shaped body includes a support section having a tubular shape with a center axis being a reference line, the support section having a proximal end and a distal end, a support substrate positioned in the support section and movable in a direction along the reference line, a needle section positioned on a main surface of the support substrate and protruding in a direction from the proximal end toward the distal end, a connecting section that detachably attaches the support substrate to the support section; and a guiding section that guides the support substrate along the reference line.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1A:
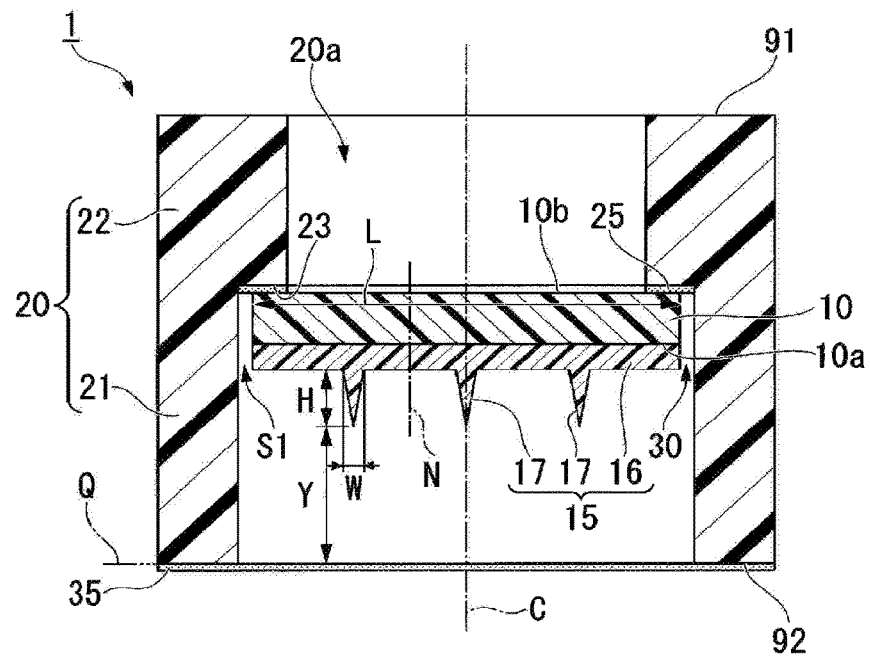
FIG. 1A is a cross-sectional side view of a needle-shaped body according to a first embodiment of the present invention.

The embodiments will now be described with reference to the accompanying drawings, wherein like reference numerals designate corresponding or identical elements throughout the various drawings.

First Embodiment

With reference to FIGS. 1A to 3, a needle-shaped body according to a first embodiment of the present invention will be described.

Figure 1B:
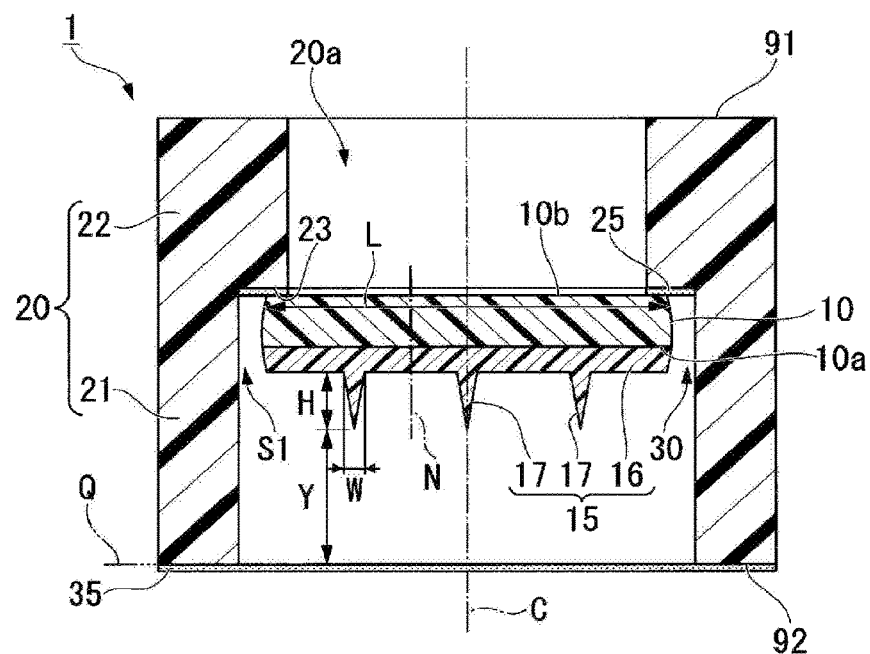
FIG. 1B is a cross-sectional side view of the needle-shaped body according to the first embodiment of the present invention.
Figure 1C:
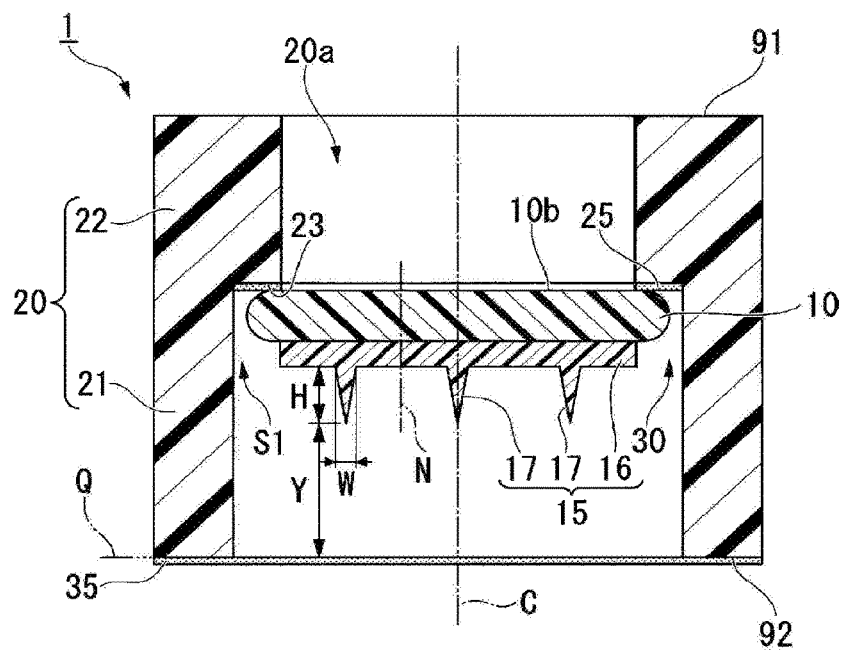
FIG. 1C is a cross-sectional side view of the needle-shaped body according to the first embodiment of the present invention.
Figure 2:
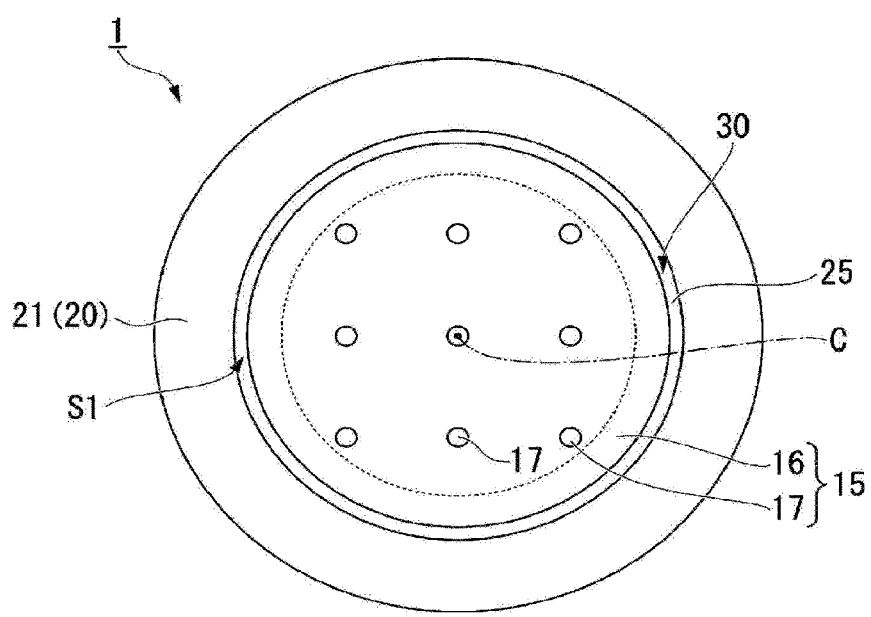
FIG. 2 is a bottom view of the needle-shaped body according to the first embodiment of the present invention.

As shown in FIGS. 1A to 2, a needle-shaped body 1 of this embodiment includes a support substrate 10, a needle section 15, a device support section (support section) 20, an adhesive member (connecting section) 25, and a guiding section 30.

The needle section 15 is provided on a first surface (main surface) 10a of the support substrate 10. The device support section (support section) 20 is formed in a cylindrical shape having a center axis as a reference line C, and has a proximal end 91 on one end and a distal end 92 on the other end. The support substrate 10 is disposed in a cylindrical hole 20a of the device support section 20, and is movable in a direction extending along the reference line C. The support substrate 10 is detachably attached to the device support section 20 via an adhesive member (connecting section) 25. The guiding section 30 guides the support substrate 10 along the reference line C relative to the device support section 20.

In the following description, a location of the needle section 15 (distal end 92) relative to the support substrate 10 is referred to as a distal side, while a location of the support substrate 10 (proximal end 91) relative to the needle section 15 is referred to as a proximal side. Throughout the drawings, the ratio of the thicknesses and dimensions of the components are adjusted for the convenience of illustration. FIG. 2 omits a protective film 35.

The support substrate 10 is formed in a disc shape having the center axis as the reference line C. A normal line N to the first surface 10a of the support substrate 10 is parallel to the reference line C. The support substrate 10 is made of a biocompatible material, and may include resins such as polypropylene and metals such as stainless steel or titanium.

The needle section 15 is a so-called microneedle (MN), and includes a base member 16 and a plurality of needle members 17 provided on the base member 16.

The base member 16 has an outer diameter equal to (or substantially equal to) an outer diameter of the support substrate 10, and has a thickness (the length in the direction of the reference line C) smaller than that of the support substrate 10.

The needle member 17 in this example is formed in a conical shape with the outer diameter decreasing toward the distal end. The needle members 17 are provided to stand on the base member 16 and extend parallel to the normal line N.

As shown in FIG. 2, the plurality of needle members 17 of this embodiment are arranged, for example, in a matrix pattern on the distal end surface of the base member 16.

As shown in FIG. 1B, a side surface of either of the support substrate 10 and the base member 16 according to this embodiment is preferably machined into a curved surface (round chamfered). The machined curved surface (round chamfering) facilitates smooth movement, allowing for sufficient transmission of a biasing force applied by a finger to the needle section for piercing into the skin. Alternatively, as shown in FIG. 1C, in this embodiment, only the support substrate may be machined into a curved surface.

As shown in FIG. 1A, a length H of the needle member 17 of this embodiment is preferably in the range of 10 μm or more and 2000 μm or less. A width W of the needle member 17 is preferably in the range of 10 μm or more and 2000 μm or less. An aspect ratio (H/W) of the height H of the needle member 17 to the width W of the needle member 17 is preferably in the range of 0.5 or more and 20 or less.

When the needle-shaped body 1 of this embodiment is pierced into the skin by hand (finger), a maximum diameter L of an outer shape of the base member 16 (a diameter when the base member 16 is a circle, a diagonal length when the base member 16 is a square, and a maximum diameter of an outer shape of the support substrate 10 in the third and fourth embodiments described below) is preferably in the range of 1 cm or more and 4 cm or less.

In addition, the needle-shaped body 1 of this embodiment can be pierced by using an applicator. In this case, the maximum diameter L of the outer shape of the base member 16 is preferably in the range of 3 mm or more and 4 cm or less.

Materials forming the base member 16 and the needle member 17 are not specifically limited as long as they have a rigidity that can be pierced into the skin, but are advantageously a poorly water soluble, biodegradable resin. Examples of such a resin include polylactic acid, polyethylene succinate, polyethylene succinate adipate, polybutylene succinate carbonate, polycaprolactone, polyester amide, polyester carbonate, or a mixture thereof.

A drug, which is not shown in the figure, is provided on a surface or the like of the needle member 17.

In this embodiment, the needle section 15 is integrally formed, for example, by an intaglio plate having a recess of a shape of the needle section 15. The needle section 15 and the support substrate 10 are securely fixed to each other via an adhesive or the like, which is not shown, with the support substrate 10 and the base member 16 being coaxially arranged.

Further, although the shape of the needle member 17 is described as a conical shape, the shape is not limited thereto. The needle member 17 may be a pyramid shape having a bottom of a triangle, rectangle, ellipse or the like. The needle member 17 may have a portion with a constant outer diameter which partially extends toward the distal end.

The arrangement pattern of the plurality of needle members 17 on the base member 16 is not limited, and the plurality of needle members 17 may be arranged in a zig-zag pattern or circular pattern. The number of needle members 17 provided on the base member 16 is not limited, and one or more needle members 17 may be provided.

As shown in FIGS. 1A to 2, the device support section 20 has a large inner diameter portion 21 and a small inner diameter portion 22 which is formed proximal to the large inner diameter portion 21 and has an inner diameter smaller than that of the large inner diameter portion 21. In other words, the device support section 20 includes the large inner diameter portion 21 which extends from the distal end 92 toward the proximal end 91 and the small inner diameter portion 22 which extends from the proximal end 91 toward the distal end 92 and has the inner diameter smaller than that of the large inner diameter portion 21. The outer diameter of the large inner diameter portion 21 is equal to the outer diameter of the small inner diameter portion 22. The large inner diameter portion 21 and the small inner diameter portion 22 are disposed on the reference line C and are offset in the direction along the reference line C.

A shoulder 23 is formed between the inner peripheral surface of the large inner diameter portion 21 and the inner peripheral surface of the small inner diameter portion 22. The distal end 92 has a reference surface Q which includes a distal end surface of the large inner diameter portion 21. The reference surface Q is perpendicular to the reference line C.

The device support section 20 is made of, for example, the same material as that of the support substrate 10 so that the large inner diameter portion 21 and the small inner diameter portion 22 are integrally formed.

The inner diameter of the large inner diameter portion 21 is slightly larger than the outer diameter of the support substrate 10, and a fine gap S1 is formed between the large inner diameter portion 21 and the support substrate 10. The foregoing guiding section 30 is formed by the inner peripheral surface of the large inner diameter portion 21 and the outer peripheral surface of the support substrate 10. Since the inner peripheral surface of the large inner diameter portion 21 guides the outer peripheral surface of the support substrate 10 in a direction along the reference line C, the support substrate 10 is guided along the reference line C relative to the device support section 20.

Further, in order to reliably guide the support substrate 10 in the direction along the reference line C, the support substrate 10 is preferably thick.

The outer diameter of the support substrate 10 is larger than the inner diameter of the small inner diameter portion 22.

The large inner diameter portion 21 has a size that can house the support substrate 10 and the needle section 15. As described below, the support substrate 10 and the needle section 15 separated from the shoulder 23 can be moved in the large inner diameter portion 21 in the direction along the reference line C.

The adhesive member 25 is formed in a ring shape, and is disposed between the shoulder 23 of the device support section 20 and the second surface 10b of the support substrate 10 so as to adhere the support substrate 10 to the shoulder 23.

The adhesive member 25 is formed by a known biocompatible adhesive having adhesion which permits separation when being subject to a pressing force by a finger.

A distance Y from the tip of the needle member 17 to the reference surface Q (see FIG. 1A) is preferably in the range of 2 mm or more and 20 cm or less. If the distance Y is less than 2 mm, the needle section 15 may be damaged by vibration during transportation or the like before it is pierced into the skin. In addition, a sufficient biasing force cannot be imparted during piercing into the skin, which may cause insufficient piercing into the skin. On the other hand, if the distance Y is over 20 cm, a movement distance of the needle member 17 during piercing into the skin increases.

The device support section 20 has an opening on the distal end of the large inner diameter portion 21, which is preferably sealed by a protective film 35 made of a known resin material. The protective film 35 has rigidity that can be pierced by the needle member 17. The protective film 35 is disposed distal to the reference surface Q.

The protective film 35 provided on the needle-shaped body 1 can prevent the needle section 15 from being inadvertently touched by a finger or the like. In addition, in the case where the inner space of the large inner diameter portion 21 is sterilized, the sterilization of the inner space of the large inner diameter portion 21 can be maintained by the support substrate 10 and the protective film 35.

Next, an effect of the needle-shaped body 1 having the above configuration will be described.

Figure 3:
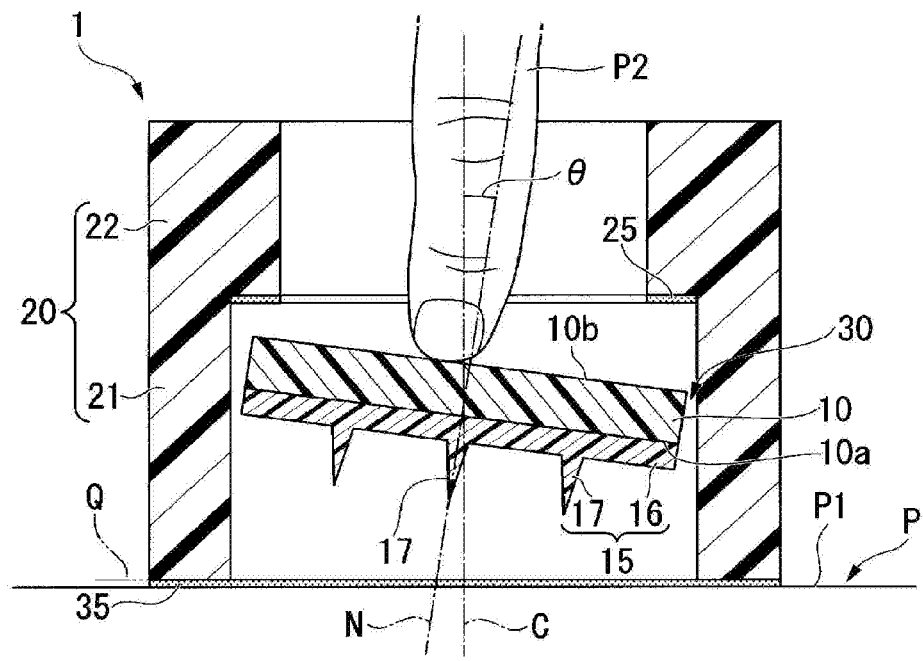
FIG. 3 is a cross-sectional side view for showing an effect of the needle-shaped body according to the first embodiment of the present invention.

As shown in FIG. 3, the protective film 35 of the needle-shaped body 1 is pressed against a skin P1 of a user P. The reference surface Q of the needle-shaped body 1 is parallel to the skin P1.

A finger P2 is inserted into an opening on the proximal end of the device support section 20 to press the second surface 10b of the support substrate 10. The support substrate 10 is separated from the adhesive member 25 when subject to a pressing force by the finger P2. Since the needle-shaped body 1 has the guiding section 30, the outer peripheral surface of the support substrate 10 is guided by the inner peripheral surface of the large inner diameter portion 21 in the direction along the reference line C. The normal line N of the support substrate 10, that is, the needle member 17 is prevented from being inclined to the reference line C when guided by the guiding section 30.

As shown in FIG. 3, in this embodiment, when an angle formed by intersection of the reference line C and the normal line N of the first surface 10a of the support substrate 10 is defined as θ, the support substrate is preferably movable in the support section along the reference line C with the angle θ within the range of 0° or more and 40° or less. More preferably, the support substrate is movable with the angle θ within the range of 0° or more and 30° or less. In this embodiment, a fine gap S1, the total thickness of the support substrate and the base member and the like are determined in order to set the angle θ within the above range.

Since the reference surface Q is perpendicular to the reference line C, the needle member 17 penetrating through the protective film 35 pierces the skin P1 in the direction perpendicular to the skin P1. A drug provided on the needle member 17 dissolves in reaction to the moisture in the skin P1 and is delivered into the skin P1.

The device support section 20 is removed while leaving the protective film 35, the needle section 15, and the support substrate 10 on the skin P1.

After a predetermined time elapsed, the protective film 35, the needle section 15, and the support substrate 10 are removed from the skin P1.

As described above, according to the needle-shaped body 1 of this embodiment, the guiding section 30 guides the support substrate 10 along the reference line C relative to the device support section 20. Accordingly, the needle section 15 can also be pierced into the skin P1 in the direction perpendicular to the skin P1 when the support substrate 10 is pressed by the finger P2 or the like.

Since the protective film 35 is provided, the needle section 15 can be prevented from being inadvertently touched by a finger P2 or the like.

Further, the distal end of the large inner diameter portion 21 of the device support section 20 can be pressed against the skin P1 of the user P to pierce the needle section 15 into the skin after the protective film 35 is separated.

In the case where the inner space of the large inner diameter portion 21 is sterilized, the sterilization of the inner space of the large inner diameter portion 21 can be maintained until immediately before the needle section 15 is pierced when the needle section 15 is pierced into the skin with the protective film 35 remaining attached as described above. Accordingly, it is further preferable to pierce the needle section 15 into the skin P1 with the protective film 35 remaining attached. In this case, the protective film needs to be sufficiently thin to the height of the needle section 15.

The protective film 35 can also be applied to the needle-shaped body according to second to fourth embodiments described below.

Moreover, in this embodiment, when the support substrate 10 is sufficiently thick, the needle section 15A may not necessarily include the base member 16, and the plurality of needle members 17 may be directly mounted to the support substrate 10 as described later in the third embodiment (see FIG. 7). In this case, the base member 16 is integrally formed with the support substrate 10.

In this embodiment, the distal end surface of the protective film 35 can be provided as the reference surface Q. In this modified example, the protective film 35 is disposed proximal to the reference surface Q, and the position of the protective film 35 relative to the reference surface Q is opposite from that of this embodiment.

Second Embodiment

Next, with reference to FIGS. 4 to 6, the second embodiment of the present invention will be described, in which the same elements as those of the above embodiment are denoted by the same reference characters. The description of the same elements is omitted, and only the difference from the above embodiment will be described.

Figure 4:
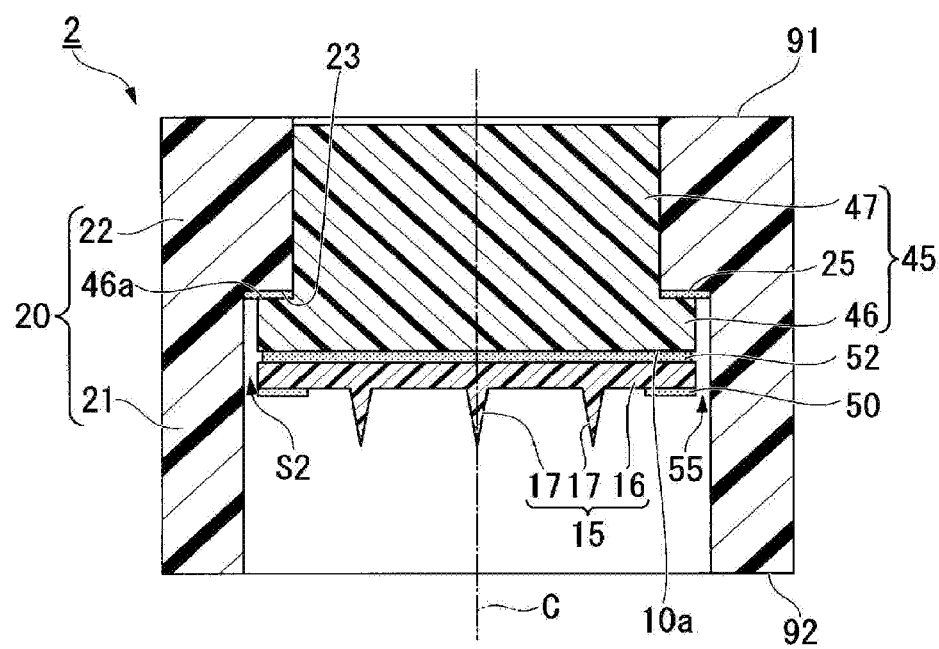
FIG. 4 is a cross-sectional side view of the needle-shaped body according to a second embodiment of the present invention.

As shown in FIG. 4, a needle-shaped body 2 according to this embodiment includes a support substrate 45, a second adhesive member 50, and a guiding section 55 instead of the support substrate 10 and the guiding section 30 of the needle-shaped body 1 of the first embodiment. In addition, this and subsequent embodiments show examples of the needle-shaped body which does not include the protective film 35.

The support substrate 45 includes a large outer diameter portion 46 disposed in the large inner diameter portion 21 and a small outer diameter portion 47 disposed in the small inner diameter portion 22 and having an outer diameter smaller than that of the large outer diameter portion 46. The large outer diameter portion 46 and the small outer diameter portion 47 are each formed in a disc shape having the center axis as the reference line C. The small outer diameter portion 47 is disposed proximal to the large outer diameter portion 46. The support substrate 45 can be made of the same material as that of the support substrate 10.

The outer diameter of the large outer diameter portion 46 is equal to the outer diameter of the base member 16. The large outer diameter portion 46 and the base member 16 are attached to each other by an auxiliary adhesive member 52 having adhesion that permits separation when the support substrate 45 picked by a finger is inclined relative to the needle section 15.

The outer diameter of the large outer diameter portion 46 is slightly smaller than the inner diameter of the large inner diameter portion 21, and a fine gap S2 is formed between the large outer diameter portion 46 and the large inner diameter portion 21. The outer diameter of the large outer diameter portion 46 is larger than the inner diameter of the small inner diameter portion 22, and a surface 46a proximal to the large outer diameter portion 46 can be engaged with the above-mentioned shoulder 23. The adhesive member 25 is disposed between the shoulder 23 of the device support section 20 and the surface 46a of the large outer diameter portion 46 so as to adhere the large outer diameter portion 46 to the shoulder 23.

A fine gap, which is not shown, is also formed between the small outer diameter portion 47 and the small inner diameter portion 22.

The above guiding section 55 is made up of the inner peripheral surface of the large inner diameter portion 21, the inner peripheral surface of the small inner diameter portion 22, and the outer peripheral surface of the large outer diameter portion 46, and the outer peripheral surface of the small outer diameter portion 47.

The second adhesive member 50 has a ring shape made of the same material as that of the adhesive member 25, for example. The second adhesive member 50 is disposed on the surface of the base member 16 on which the plurality of needle members 17 so as to surround the plurality of needle members 17.

The adhesion of the second adhesive member 50 is higher than that of the auxiliary adhesive member 52.

Next, an effect of the needle-shaped body 2 having the above configuration will be described.

Figure 5:
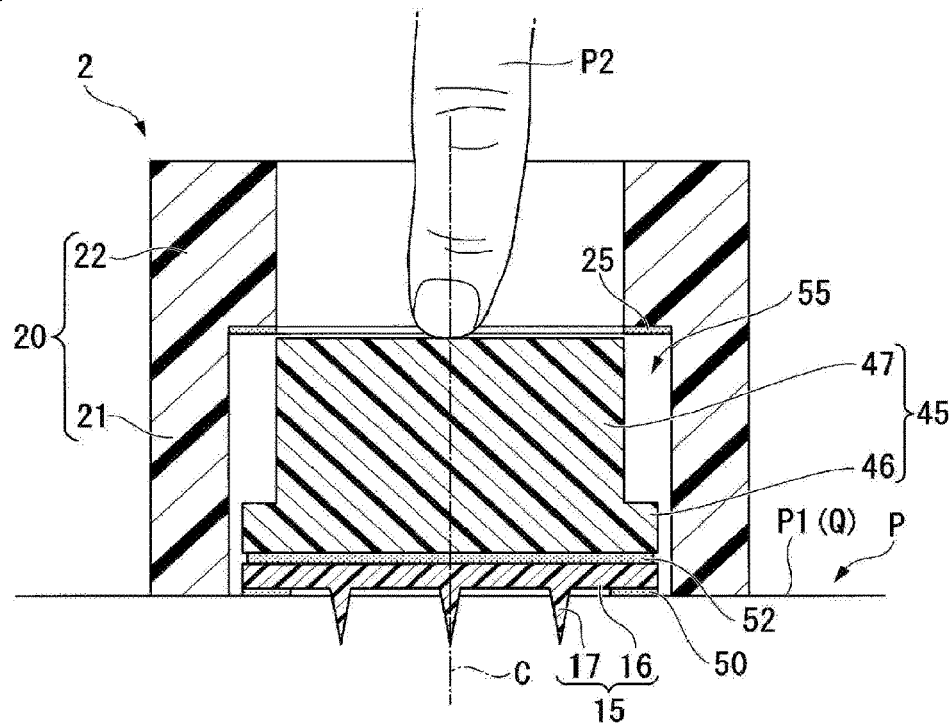
FIG. 5 is a cross-sectional side view for showing an effect of the needle-shaped body according to the second embodiment of the present invention.

As shown in FIG. 5, the distal end surface of the device support section 20 of the needle-shaped body 2 is pressed against the skin P1 of the user P. The reference surface Q of the needle-shaped body 2 conforms to the skin P1.

The finger P2 is inserted into an opening on the proximal end of the device support section 20 to press the small outer diameter portion 47. The large outer diameter portion 46 is separated from the adhesive member 25 when subject to a pressing force by the finger P2. Since the needle-shaped body 2 has the guiding section 55, the outer peripheral surface of the large outer diameter portion 46 is guided by the inner peripheral surface of the large inner diameter portion 21 in the direction along the reference line C and the outer peripheral surface of the small outer diameter portion 47 is guided by the inner peripheral surface of the small inner diameter portion 22 in the direction along the reference line C.

In this embodiment, when an angle formed by intersection of the reference line C and the normal line N of the first surface 10a of the support substrate 10 is defined as θ, the support substrate is preferably movable in the support section along the reference line C with the angle θ within the range of 0° or more and 40° or less. More preferably, the support substrate is movable with the angle θ within the range of 0° or more and 30° or less. In this embodiment, the size, thickness and the like of the small outer diameter portion 47 and the large outer diameter portion 46 are determined relative to the device support section 20 in order to set the angle θ within the above range.

Since the reference surface Q is perpendicular to the reference line C, the needle member 17 pierces the skin P1 in the direction perpendicular to the skin P1. At this time, the second adhesive member 50 is adhered to the skin P1.

The device support section 20 is removed while leaving the second adhesive member 50, the needle section 15, the auxiliary adhesive member 52, and the support substrate 45 adhered to the skin P1.

Figure 6:
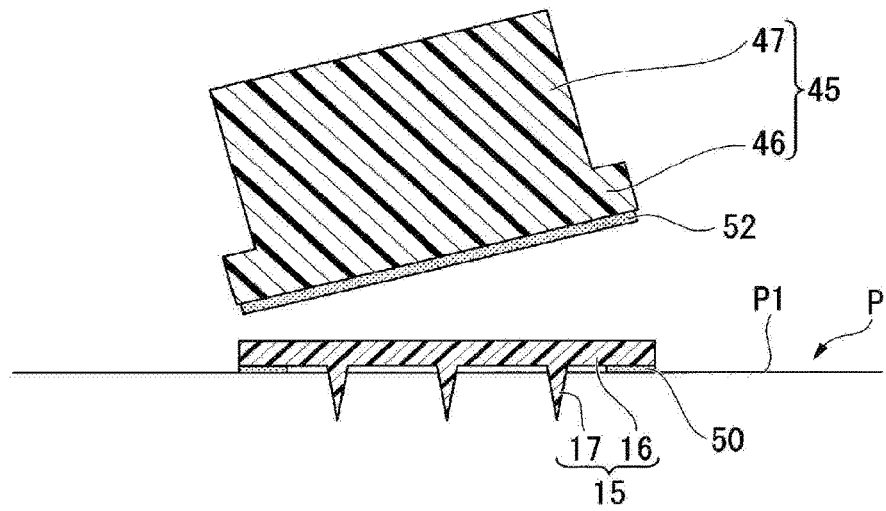
FIG. 6 is a cross-sectional side view for showing an effect of the needle-shaped body according to the second embodiment of the present invention.

As shown in FIG. 6, the needle section 15 is separated from the auxiliary adhesive member 52 when the small outer diameter portion 47 of the support substrate 45 is picked by the finger P2, which is not shown, and the support substrate 45 is inclined relative to the needle section 15.

After a predetermined time elapsed, the second adhesive member 50 and the needle section 15 are removed from the skin P1.

As described above, the needle-shaped body 2 of this embodiment can also pierce the skin P1 in the direction perpendicular to the skin P1 when the support substrate 45 is pressed by the finger P2 or the like.

Moreover, the device support section 20 includes the large inner diameter portion 21 and the small inner diameter portion 22, and the support substrate 45 includes the large outer diameter portion 46 and the small outer diameter portion 47. Accordingly, the support substrate 45 can be guided more accurately relative to the device support section 20 along the reference line C since the guidance is performed by each of the large inner diameter portion 21 and the large outer diameter portion 46, and the small inner diameter portion 22 and the small outer diameter portion 47.

Third Embodiment

Next, with reference to FIGS. 7A to 12, the third embodiment of the present invention will be described, in which the same elements as those of the above embodiments are denoted by the same reference characters. The description of the same elements is omitted, and only the difference from the above embodiments will be described.

Figure 7A:
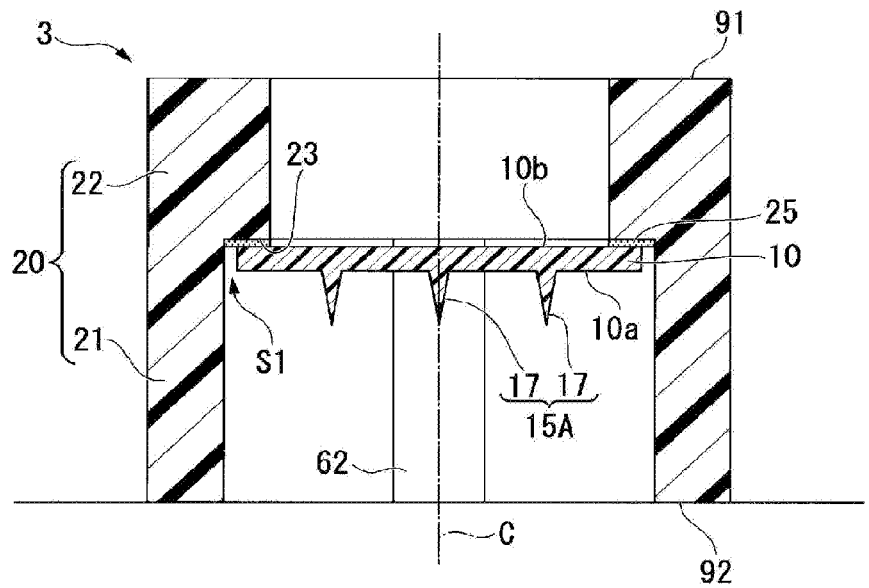
FIG. 7A is a cross-sectional side view of the needle-shaped body according to a third embodiment of the present invention.
Figure 7B:
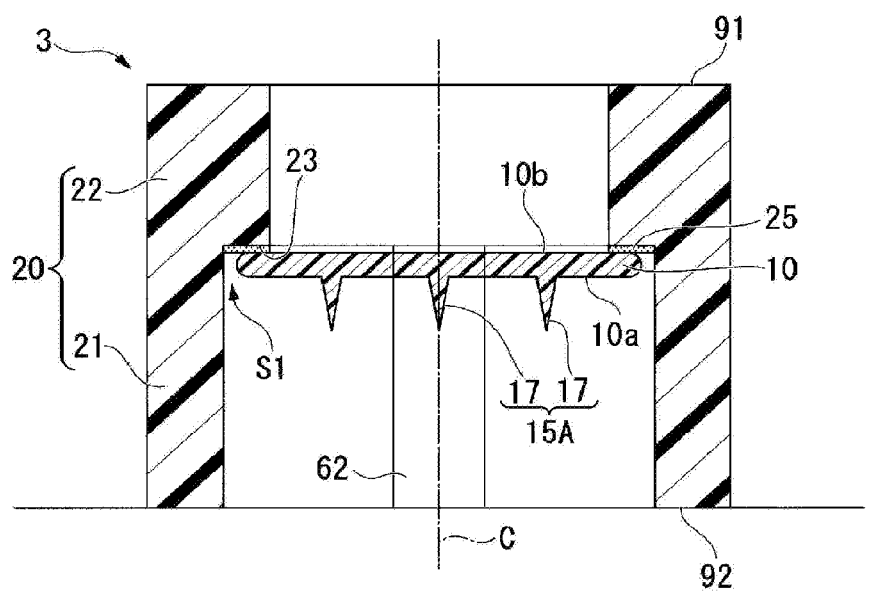
FIG. 7B is a cross-sectional side view of the needle-shaped body according to the third embodiment of the present invention.
Figure 8:
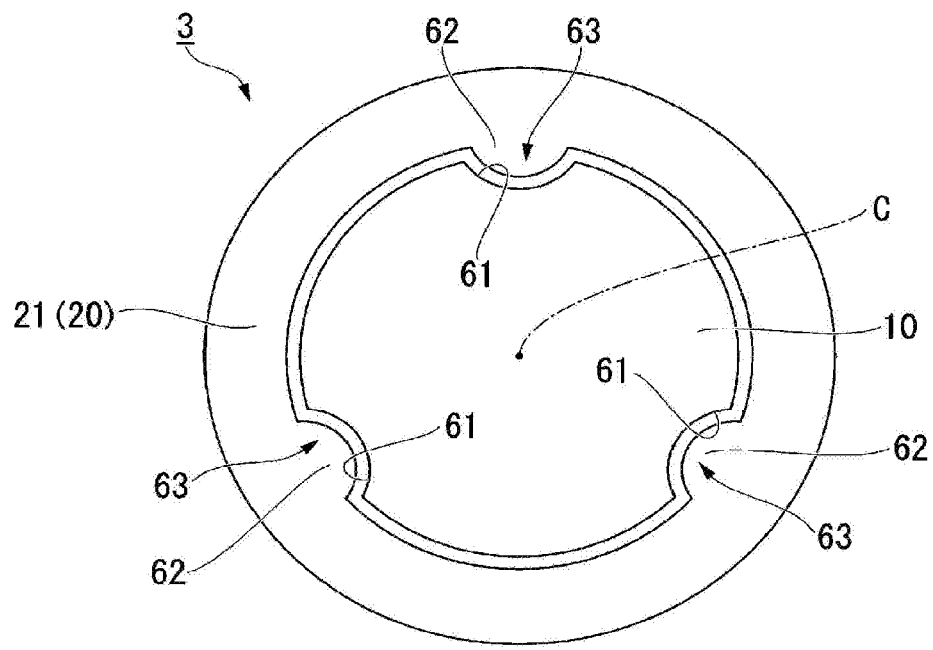
FIG. 8 is a cross-sectional plan view of the needle-shaped body according to the third embodiment of the present invention.

As shown in FIGS. 7A to 8, a needle-shaped body 3 according to this embodiment includes a recess (engaging section) 61 extending in a direction along the reference line C on the outer peripheral surface of the support substrate 10 of the needle-shaped body 1 according to the first embodiment, and a protrusion (engaged section) 62 extending in a direction along the reference line C on the inner peripheral surface of the large inner diameter portion 21 of the device support section 20 so as to engage with the recess 61.

Further, a guiding section 63 is formed by the recess 61 and the protrusion 62. In other words, the guiding section 63 may include the inner peripheral surface of the large inner diameter portion 21 and the outer peripheral surface of the support substrate 10 in addition to the recess 61 and the protrusion 62.

In the cross section shown in FIG. 8 which is perpendicular to the reference line C, the recess 61 of the support substrate 10 is formed recessed in a semi-circular shape from the outer peripheral surface of the support substrate 10. Three recesses 61 are formed on the support substrate 10 about the reference line C.

On the other hand, the protrusion 62 on the large inner diameter portion 21 is formed protruding in a semi-circular shape from the inner peripheral surface of the large inner diameter portion 21. Three protrusions 62 are formed on the large inner diameter portion 21 about the reference line C corresponding to the recesses 61. Each of the three recesses 61 and the three protrusions 62 are preferably formed about the reference line C with an equal pitch.

In this embodiment, the gap S1 between the large inner diameter portion 21 and the support substrate 10 may be fine or large. The reason for that is the engagement between the recess 61 and the protrusion 62 is sufficient to guide the support substrate 10 along the reference line C relative to the device support section 20 as described below.

In this example, the needle section 15A does not include the base member 16, and the plurality of needle members 17 are directly mounted to the support substrate 10.

In the needle-shaped body 3 having the above configuration, when the second surface 10b of the support substrate 10 is pressed by the finger P2, which is not shown, the support substrate 10 is separated from the adhesive member 25 by a pressing force applied by the finger P2.

The protrusion 62 of the guiding section 63 guides the recess 61 along the reference line C. In other words, the support substrate 10 is guided along the reference line C relative to the device support section 20.

In this embodiment, when an angle formed by intersection of the reference line C and the normal line N of the first surface 10a of the support substrate 10 is defined as θ, the support substrate is preferably movable in the support section along the reference line C with the angle θ within the range of 0° or more and 40° or less. More preferably, the support substrate is movable with the angle θ within the range of 0° or more and 30° or less. In this embodiment, the fine gap S1, the total thickness of the support substrate 10 and the base member 16 and the like are determined in order to set the angle θ within the above ranges.

As shown in FIG. 7B, a side surface of the support substrate 10 according to this embodiment is preferably machined into a curved surface (round chamfered). The machined curved surface (round chamfering) of the side surface of the support substrate 10 facilitates smooth movement, allowing for sufficient transmission of a biasing force applied by a finger to the needle section for piercing into the skin.

As described above, the needle-shaped body 3 of this embodiment can also pierce the skin P1 in the direction perpendicular to the skin P1 when the support substrate 45 is pressed by the finger P2 or the like.

Further, in this embodiment, the three recesses 61 are formed on the support substrate 10 and the three protrusions 62 are formed on the large inner diameter portion 21. However, the number of recesses 61 formed on the support substrate 10, and the number of protrusions 62 formed on the large inner diameter portion 21 are not limited as long as they are the same, and may be one, two or four or more.

The configurations of the engaging section and the engaged section of this embodiment may be various as described below.

Figure 9:
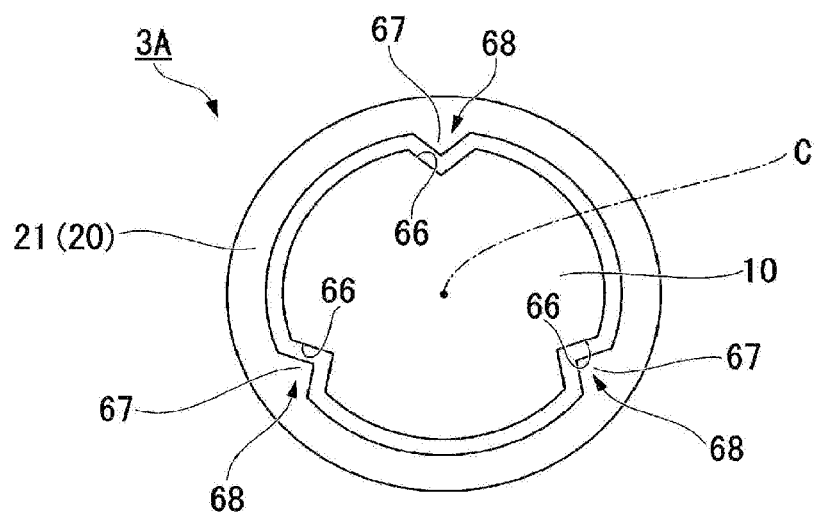
FIG. 9 is a cross-sectional plan view of the needle-shaped body according to a modified example of the present invention.

A needle-shaped body 3A shown in FIG. 9 may have a recess (engaging section) 66 recessed from the outer peripheral surface of the support substrate 10 in a triangular shape and a protrusion (engaged section) 67 protruding from the inner peripheral surface of the large inner diameter portion 21 in a triangular shape in the cross section perpendicular to the reference line C.

Further, a guiding section 68 is formed by the recess 66 and the protrusion 67.

Besides this embodiment and the modified example, the shape of the recess formed on the support substrate 10 and the shape of the protrusion formed on the large inner diameter portion 21 are not limited, and may be a polygonal shape such as rectangle or a semi-elliptical shape in the cross section described above.

Figure 10:
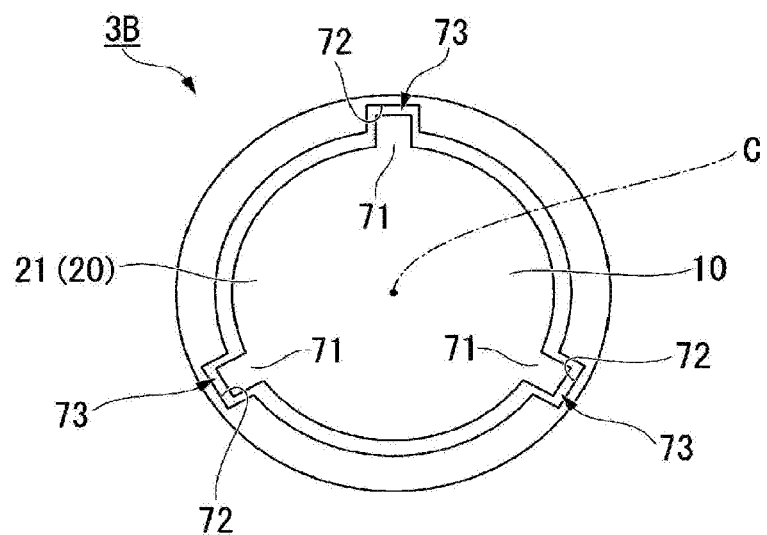
FIG. 10 is a cross-sectional plan view of the needle-shaped body according to another modified example of the present invention.

A needle-shaped body 3B shown in FIG. 10 may have a protrusion (engaging section) 71 protruding from the outer peripheral surface of the support substrate 10 in a rectangular shape and a recess (engaged section) 72 recessed from the inner peripheral surface of the large inner diameter portion 21 in a rectangular shape in the cross section described above.

Further, a guiding section 73 is formed by the protrusion 71 and the recess 72.

Figure 11:
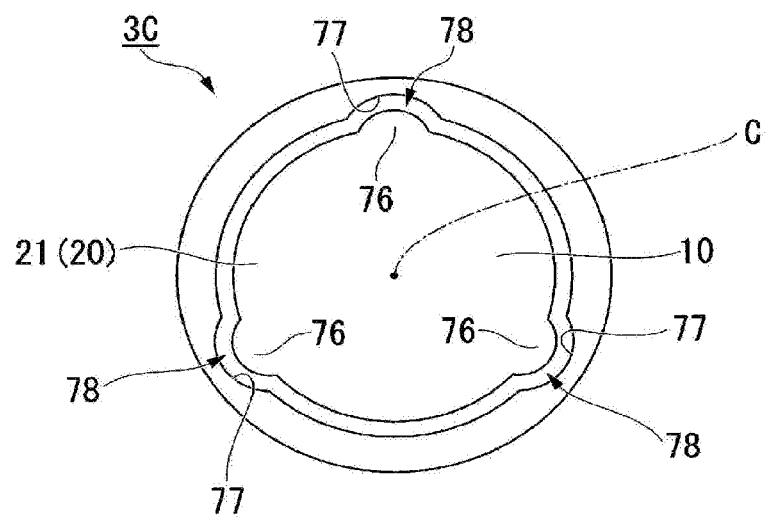
FIG. 11 is a cross-sectional plan view of the needle-shaped body faccording to another modified example of the present invention.

A needle-shaped body 3C shown in FIG. 11 may have a protrusion (engaging section) 76 protruding from the outer peripheral surface of the support substrate 10 in a semi-circular shape and a recess (engaged section) 77 recessed from the inner peripheral surface of the large inner diameter portion 21 in a semi-circular shape in the cross section described above.

Further, a guiding section 78 is formed by the protrusion 76 and the recess 77.

Figure 12:
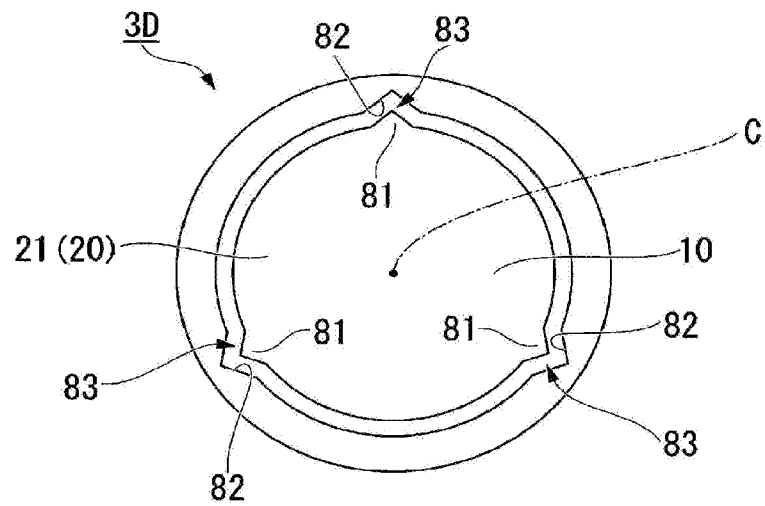
FIG. 12 is a cross-sectional plan view of the needle-shaped body according to another modified example of the present invention.

A needle-shaped body 3D shown in FIG. 12 may have a protrusion (engaging section) 81 protruding from the outer peripheral surface of the support substrate 10 in a triangular shape and a recess (engaged section) 82 recessed from the inner peripheral surface of the large inner diameter portion 21 in a triangular shape in the cross section described above.

Further, a guiding section 83 is formed by the protrusion 81 and the recess 82.

Besides these modified examples, the protrusion formed on the support substrate 10 and the recess formed on the large inner diameter portion 21 may be any shape, including a polygonal shape such as hexagon or a semi-elliptical shape in the cross section described above.

Fourth Embodiment

Next, with reference to FIGS. 13 to 15, the fourth embodiment of the present invention will be described, in which the same elements as those of the above embodiments are denoted by the same reference characters. The description of the same elements is omitted, and only the difference from the above embodiments will be described.

Figure 13:
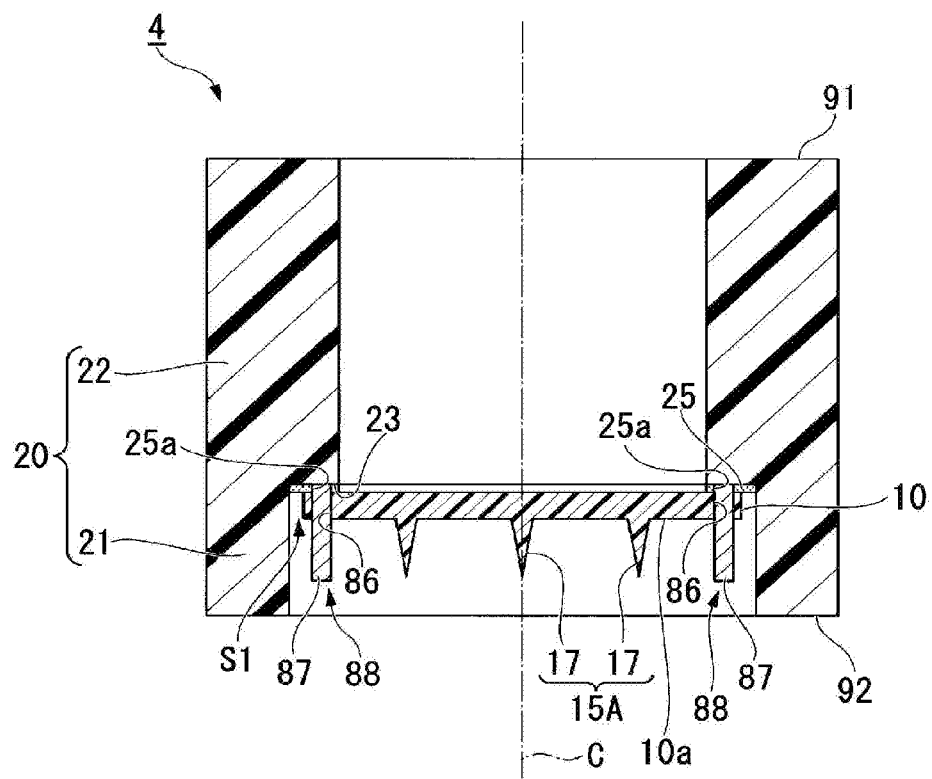
FIG. 13 is a cross-sectional side view of the needle-shaped body according to a fourth embodiment of the present invention.
Figure 14:
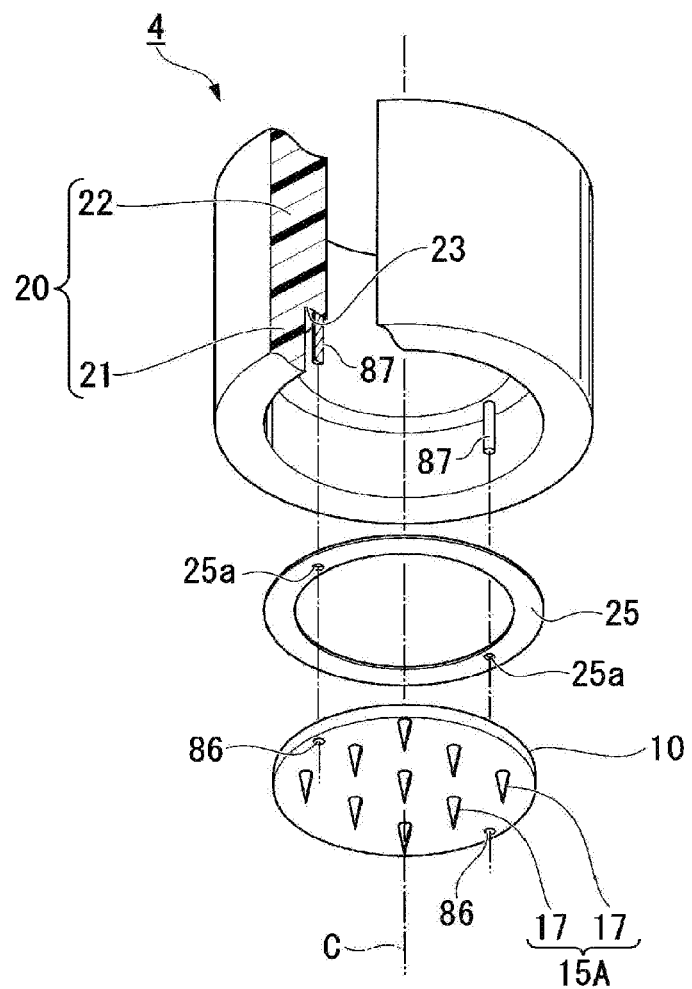
FIG. 14 is an exploded, partially cutaway perspective view of the needle-shaped body according to the fourth embodiment of the present invention.

As shown in FIGS. 13 and 14, a needle-shaped body 4 according to this embodiment includes a needle section 15A instead of the needle section 15 of the needle-shaped body 1 of the first embodiment. A through hole 86 is formed on the support substrate 10 of the needle-shaped body 4 so as to extend in the direction along the reference line C. In the device support section 20 of the needle-shaped body 4, a support pin (shaft member) 87 extending in the direction along the reference line C is inserted in the through hole 86.

Further, a guiding section 88 is formed by the through hole 86 and the support pin 87.

Two through holes 86 are formed about the reference line C on the support substrate 10. Two communication holes 25a are formed on the adhesive member 25 so as to communicate with the through holes 86 of the support substrate 10.

The support pin 87 is formed in a columnar shape made of, for example, the same material as that of the device support section 20.

The proximal end of the support pin 87 is attached on the shoulder 23 via an adhesive or the like, which is not shown. Two support pins 87 corresponding to the through holes 86 are formed about the reference line C.

The support pin 87 is movable in a direction along the reference line C in the through hole 86 of the support substrate 10.

In this embodiment, the gap S1 between the large inner diameter portion 21 and the support substrate 10 may be fine or large. The reason for that is the insertion of the support pin 87 into the through hole 86 is sufficient to guide the support substrate 10 along the reference line C relative to the device support section 20 as described below.

Figure 15:
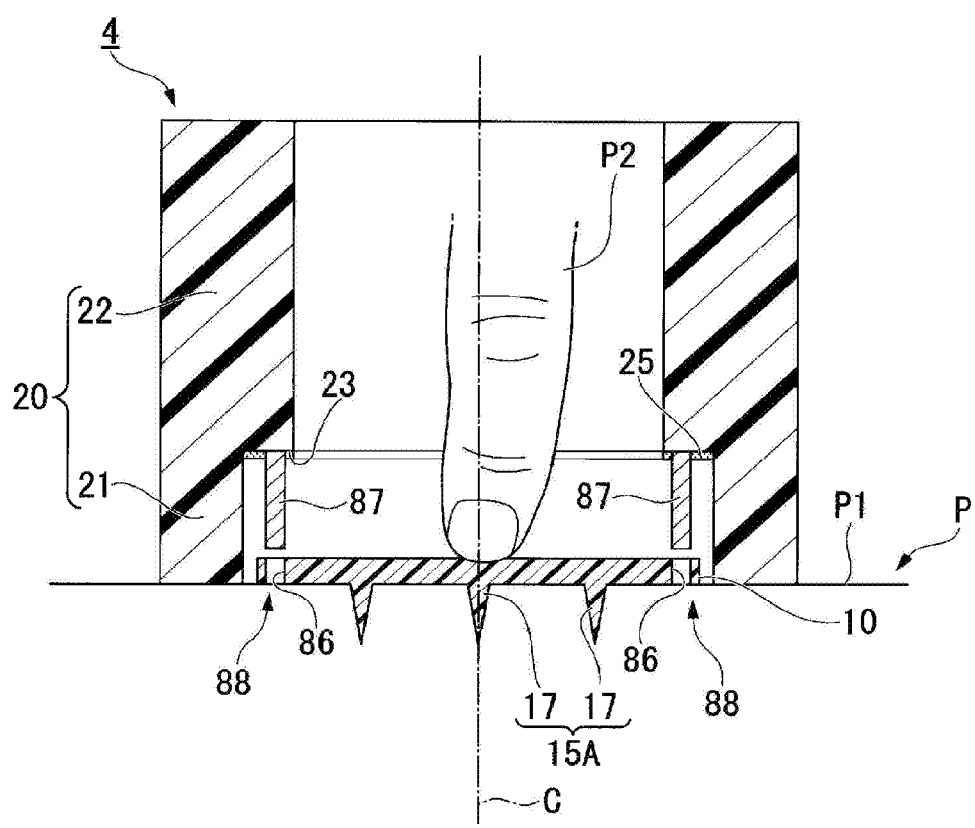
FIG. 15 is a cross-sectional side view for showing an effect of the needle-shaped body according to the fourth embodiment of the present invention.

In the needle-shaped body 4 having the above configuration, as shown in FIG. 15, the distal end surface of the device support section 20 of the needle-shaped body 4 is pressed against the skin P1 of the user P.

When the second surface 10b of the support substrate 10 is pressed by the finger P2, the support substrate 10 is separated from the adhesive member 25 by a pressing force of the finger P2.

The through hole 86 is guided by the support pin 87 of the guiding section 88 along the reference line C. In other words, the support substrate 10 is guided along the reference line C relative to the device support section 20.

When an angle formed by intersection of the reference line C and the normal line N of the first surface 10a of the support substrate 10 is defined as θ, the support substrate is preferably movable in the support section along the reference line C with the angle θ within the range of 0° or more and 40° or less. More preferably, the support substrate is movable with the angle θ within the range of 0° or more and 30° or less. In this embodiment, an inner diameter of the through hole 86 and an outer diameter of the support pin 87 are determined in order to set the angle θ within the above range.

As described above, the needle-shaped body 4 of the fourth embodiment can also pierce the skin P1 in the direction perpendicular to the skin P1 when the support substrate 10 is pressed by the finger P2 or the like.

Further, although the support pin 87 is described as columnar shape in this embodiment, the support pin 87 may be in any shape. A pillar shape or a tubular shape having a bottom of an elliptical shape or a polygonal shape may be used.

In this embodiment, two through holes 86 may be formed on the support substrate 10, and two support pins 87 are formed on the shoulder 23 of the device support section 20. However, the number of the through holes 86 formed on the support substrate 10, and the number of the support pins 87 formed on the device support section 20 are not limited as long as they are the same, and may be one, or three or more.

The first embodiment to the fourth embodiment of the present invention have been described in detail with reference to the drawings. However, the specific configuration is not limited to these embodiments. Various modifications, combinations, and deletion of the configurations may be included without departing from the principle of the present invention. Of course, each of the configurations shown in the embodiments can be appropriately combined for use.

For example, in the first embodiment to the fourth embodiment, the device support section 20 is formed in a cylindrical shape. However, the tubular shape of this embodiment is not limited to a circular cylindrical shape, and may be a tubular shape having a cross section which is a plane perpendicular to the reference line C with the outline of an elliptical or polygonal shape.

In the first, third, and fourth embodiments, the needle-shaped body preferably includes the second adhesive member 50 of the second embodiment.

Further, the needle-shaped body is capable of piercing the needle section into the skin with a finger. Moreover, the needle-shaped body is capable of piercing the needle section into the skin by using an applicator. The needle-shaped body is not limited to the piercing method.

According to the needle-shaped body described in PTL 1, the substrate is pressed, for example, by a finger of a user while the needle section is placed closer to the skin than the substrate is, to thereby pierce the needle section into the skin. Although this technique of piercing the needle section with a finger is an easy operation, the needle section is sometimes pierced in an oblique direction relative to the skin when the substrate is pressed. As a result of this, the depth of the drug administered in the skin varies, leading to variation in drug effect due to the position or oblique angle of the needle section disposed on the substrate.

In order to address the problem, the needle-shaped body is mounted in a tubular applicator, which is a piercing assistance device, and the substrate is pushed into the applicator while the distal end of the applicator is pressed against the skin. As a result of this, since the substrate is pushed into the applicator along the axis of the applicator, the needle section is pierced in a direction perpendicular to the skin.

Accordingly, a depth of the drug administered in the skin becomes substantially constant, and the drug effect is stabilized.

However, an operation of mounting the needle-shaped body in the applicator is complicated. Therefore, there is a need for piercing of the needle section in a direction perpendicular to the skin even without using an applicator.

The present invention has an aspect to provide a needle-shaped body that can be pierced in a direction perpendicular to the skin even by pressing the support substrate with a finger or the like.

A needle-shaped body according to a first aspect of the present invention includes: a support section formed in a tubular shape having a center axis as a reference line, the support section having a proximal end and a distal end; a support substrate disposed in the support section and movable in a direction along the reference line; a needle section disposed on a main surface of the support substrate, the needle section protruding in a direction from the proximal end toward the distal end; a connecting section that detachably attaches the support substrate to the support section; and a guiding section that guides the support substrate along the reference line relative to the support section.

In the first aspect, it is preferred that the support section includes: a large inner diameter portion which extends from the distal end toward the proximal end; and a small inner diameter portion which extends from the proximal end toward the distal end and has an inner diameter smaller than the inner diameter of the large inner diameter portion, the support substrate includes: a large outer diameter portion disposed in the large inner diameter portion; and a small outer diameter portion having an outer diameter smaller than the outer diameter of the large outer diameter portion and disposed in the small inner diameter portion, and the guiding section is formed by the inner peripheral surfaces of the large inner diameter portion and the small inner diameter portion and the outer peripheral surfaces of the large outer diameter portion and the small outer diameter portion.

In the first aspect, it is preferred that the outer peripheral surface of the support substrate is provided with an engaging section which extends in a direction along the reference line, the inner peripheral surface of the support section is provided with an engaged section which extends in a direction along the reference line and engages with the engaging section, and the guiding section is formed by the engaging section and the engaged section.

In the first aspect, it is preferred that the support substrate has a through hole formed in a direction along the reference line, the support section is provided with a shaft member which extends in a direction along the reference line and which is inserted in the through hole, and the guiding section is formed by the through hole and the shaft member.

The needle-shaped body according to the first aspect may include a protective film that seals an opening on the distal end of the support section.

In the needle-shaped body according to the above aspects of the present invention, piercing in a direction perpendicular to the skin can be achieved even by pressing the support substrate with a finger or the like.

REFERENCE SIGNS LIST 1, 2, 3, 3A, 3B, 3C, 3D, 4 needle-shaped body
10, 45 support substrate
10a first surface (main surface)
15 needle section
20 device support section (support section)
20a cylindrical hole
21 large inner diameter portion
22 small inner diameter portion
25 adhesive member (connecting section)
30, 55, 63, 68, 73, 78, 83, 88 guiding section
35 protective film
46 large outer diameter portion
47 small outer diameter portion
61, 66 recess (engaging section)
62, 67 protrusion (engaged section)
71, 76, 81 protrusion (engaging section)
72, 77, 82 recess (engaged section)
86 through hole
87 support pin (shaft member)
91 proximal end
92 distal end
C reference line Obviously, numerous modifications and variations of the present invention are possible in light of the above teachings. It is therefore to be understood that within the scope of the appended claims, the invention may be practiced otherwise than as specifically described herein.

What is claimed is:

1. A needle-shaped body, comprising:
   a support section having a tubular shape with a center axis, a proximal end, and a distal end;
   a support substrate positioned in the support section and movable in a direction along the center axis;
   a needle section positioned on a main surface of the support substrate and protruding in a direction from the proximal end toward the distal end; and
   a connecting section detachably attaching the support substrate to the support section,
   wherein the support section includes a large inner diameter portion extending from the distal end toward the proximal end, and a small inner diameter portion extending from the proximal end toward the distal end and having an inner diameter smaller than an inner diameter of the large inner diameter portion, the support substrate has an outer peripheral surface that includes an engaging section extending in a direction along the center axis of the support section, the large inner diameter portion of the support section has an inner peripheral surface including an engaged section extending in the direction along the center axis and engaging with the engaging section of the support substrate, the engaging section and the engaged section form a guiding section configured to guide the support substrate along the center axis of the support section, and the support substrate is movable in the support section along the center axis of the support section within a range of an angle $\theta$ being from 0° to 40°, where $\theta$ is an angle formed by the center axis of the support section intersecting a normal line of the main surface of the support substrate.

2. The needle-shaped body according to claim 1, wherein the support substrate includes a large outer diameter portion positioned in the large inner diameter portion of the support section, and a small outer diameter portion positioned in the small inner diameter portion of the support section and having an outer diameter smaller than an outer diameter of the large outer diameter portion such that the support substrate is movable in the support section along the center axis of the support section within the range of the angle $\theta$ being from 0° to 40°.

3. The needle-shaped body according to claim 1, wherein the support substrate has a through hole formed in a direction along the center axis of the support section, and the support section includes a shaft member which extends in a direction along the center axis of the support section and is positioned in the through hole such that the support substrate is movable in the support section along the center axis of the support section within the range of the angle $\theta$ being from 0° to 40°.

4. The needle-shaped body according to claim 1, further comprising:
   a protective film positioned over an opening on the distal end of the support section.

5. The needle-shaped body according to claim 2, further comprising:
   a protective film positioned over an opening on the distal end of the support section.

6. The needle-shaped body according to claim 3, further comprising:
   a protective film positioned over an opening on the distal end of the support section.

7. The needle-shaped body according to claim 1, wherein the support substrate has a curved side surface forming the engaging section.

8. The needle-shaped body according to claim 1, wherein the needle section includes a base member and a plurality of needle members formed on the base member, and the base member has a curved side surface forming the engaging section.

9. The needle-shaped body according to claim 2, wherein the needle section includes a base member and a plurality of needle members formed on the base member, and the base member has a curved side surface forming the engaging section.

10. The needle-shaped body according to claim 3, wherein the needle section includes a base member and a plurality of needle members formed on the base member, and the base member has a curved side surface forming the engaging section.

11. The needle-shaped body according to claim 1, wherein the support substrate is movable in the support section along the center axis of the support section within a range of the angle θ being from 0° to 30°.

12. The needle-shaped body according to claim 2, wherein the support substrate is movable in the support section along the center axis of the support section within a range of the angle θ being from 0° to 30°.

13. The needle-shaped body according to claim 3, wherein the support substrate is movable in the support section along the center axis of the support section within a range of the angle θ being from 0° to 30°.

14. The needle-shaped body according to claim 1, wherein the engaging section is a recess, and the engaged section is a protrusion such that the protrusion engages with the recess.

15. The needle-shaped body according to claim 1, wherein the engaging section is a protrusion, and the engaged section is a recess such that the protrusion engages with the recess.

16. The needle-shaped body according to claim 7, further comprising:
   a protective film positioned over an opening on the distal end of the support section.

17. The needle-shaped body according to claim 8, wherein the support substrate is movable in the support section along the center axis of the support section within a range of the angle θ being from 0° to 30°.

18. The needle-shaped body according to claim 7, wherein the support substrate is movable in the support section along the center axis of the support section within a range of the angle θ being from 0° to 30°.

19. The needle-shaped body according to claim 14, wherein the needle section includes a base member and a plurality of needle members formed on the base member, and the base member has a curved side surface forming the engaging section.

20. The needle-shaped body according to claim 15, wherein the needle section includes a base member and a plurality of needle members formed on the base member, and the base member has a curved side surface forming the engaging section.

* * * * *